(12) United States Patent
Taylor et al.

(10) Patent No.: US 10,039,474 B2
(45) Date of Patent: Aug. 7, 2018

(54) SYSTEM FOR TRACKING MICROSURGICAL INSTRUMENTATION

(71) Applicant: THE JOHNS HOPKINS UNIVERSITY, Baltimore, MD (US)

(72) Inventors: Russell H. Taylor, Severna Park, MD (US); Marcin Arkadiusz Balicki, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 14/165,972

(22) Filed: Jan. 28, 2014

(65) Prior Publication Data
US 2014/0213892 A1 Jul. 31, 2014

Related U.S. Application Data

(60) Provisional application No. 61/757,540, filed on Jan. 28, 2013.

(51) Int. Cl.
*A61B 5/06* (2006.01)
*A61B 34/20* (2016.01)

(52) U.S. Cl.
CPC ............. *A61B 5/061* (2013.01); *A61B 34/20* (2016.02); *A61B 2034/2055* (2016.02)

(58) Field of Classification Search
CPC combination set(s) only.
See application file for complete search history.

(56) References Cited

U.S. PATENT DOCUMENTS

| | | | | |
|---|---|---|---|---|
| 4,665,914 A | * | 5/1987 | Tanne | A61B 3/1005 600/558 |
| 5,938,674 A | * | 8/1999 | Terry | A61F 9/013 606/161 |
| 2006/0247517 A1 | * | 11/2006 | Labadie | A61B 5/06 600/426 |

(Continued)

FOREIGN PATENT DOCUMENTS

| | | |
|---|---|---|
| WO | 2002/064031 A2 | 8/2002 |
| WO | 2012/149548 A2 | 11/2012 |

OTHER PUBLICATIONS

Pitcher, J., et al., "Robotic Eye Surgery: Past, Present, and Future", J Comput Sci Syst Biol (2012) S3.
(Continued)

*Primary Examiner* — Serkan Akar
*Assistant Examiner* — Farshad Negarestan
(74) *Attorney, Agent, or Firm* — Johns Hopkins Technology Ventures

(57) ABSTRACT

An embodiment in accordance with the present invention provides a tracking system architecture for tracking surgical tools in a surgical field. The system architecture is integrated into a mask placed directly on the face of the patient. The system can combine multiple imaging and range finding technologies for tracking the eye and the surgical instrumentation. The system can be used to generate a three dimensional scene for use during the surgical procedure. Additionally, the system can incorporate a modular design to account for variable anatomy. The system described is for eye surgery applications. However, the system could also be used for other procedures such as cochlear implant or craniotomy.

13 Claims, 2 Drawing Sheets

(56) References Cited

U.S. PATENT DOCUMENTS

| | | | |
|---|---|---|---|
| 2010/0081914 A1* | 4/2010 | Waynik | A61B 19/5244 |
| | | | 600/407 |
| 2012/0143049 A1* | 6/2012 | Neubauer | A61B 34/20 |
| | | | 600/424 |
| 2015/0254964 A1* | 9/2015 | Raichman | G08B 21/245 |
| | | | 340/573.1 |

OTHER PUBLICATIONS

Maclachlan, R., et al., "High-Speed Microscale Optical Tracking Using Digital Frequency-Domain Multiplexing", IEEE Trans Instrum Meas. Jun. 1, 2009, vol. 58, No. 6, pp. 1991-2001.

* cited by examiner

SYSTEM FOR TRACKING MICROSURGICAL INSTRUMENTATION

CROSS REFERENCE TO RELATED APPLICATION

This application claims the benefit of U.S. Provisional Patent Application No. 61/757,540 filed on Jan. 28, 2013, which is incorporated by reference, herein, in its entirety.

GOVERNMENT SUPPORT

This invention was made with government support under grant 1R01EB007969-01 awarded by the National Institutes of Health and EEC-9731478 awarded by the National Science Foundation. The government has certain rights in the invention.

FIELD OF THE INVENTION

The present invention relates generally to surgery. More particularly the present invention relates to a system for tracking microsurgical instrumentation during a procedure.

BACKGROUND OF THE INVENTION

Computer and robot assisted eye surgery has great potential to improve upon eye surgery and to address common problems encountered in many eye surgery tasks. Common problems encountered in the eye surgery context include poor visualization, lack of force sensing, hand tremor, accessibility, etc. Robotic manipulators can provide the needed stability and precision, especially in delicate tasks such as retinal membrane peeling. Micro-force sensors can offer information that is currently not available through conventional means. Additionally, eye surgery would benefit from positional feedback of surgical instruments relative to the eye. However, this information regarding position of surgical instruments relative to the eye is not currently available. Such information can be used to prevent undesirable collisions, improvement of remote center of motion tracking including assessment of surgical skill through analysis of instrument motion, recording of surgical procedures for education and for safety monitoring to ensure the execution of standard protocols, like the administration of a corneal lubricant.

It would therefore be advantageous to provide a system for real-time tracking of the eye and the surgical instruments relative to each other and the eye during surgical procedures.

SUMMARY OF THE INVENTION

The foregoing needs are met, to a great extent, by the present invention, wherein in one aspect a system for tracking microsurgical instrumentation includes a platform configured to sit at a surgical site on a patient. The system includes a sensor positioned on the platform and configured to receive information regarding the surgical site and also configured to transmit said information regarding the surgical site. Additionally, the system includes a computing device configured to receive the information regarding the surgical site transmitted by the sensor.

In accordance with an aspect of the present invention the system can include multiple sensors. If multiple sensors are used they can be positioned about the platform to create redundancy in the transmitted information. The system can be used for eye surgery, cochlear implant surgery, craniotomy or any other surgery for which such a system would be useful to one of skill in the art. If an eye surgery is being performed the platform can take the form of an eye mask. A system for eye surgery could also include an eye retractor.

In accordance with another aspect of the present invention, the system can include an attachment point for a surgical robot. Additionally, the system can include a finger rest to aid in the reduction of tremor and hand fatigue. Further, the computing device is further configured to provide three-dimensional feedback regarding the surgical site.

In accordance with another aspect of the present invention, a method for tracking microsurgical instrumentation at a surgical site includes gathering data about the microsurgical instrumentation at the surgical site with a sensor positioned adjacent to the surgical site and transmitting data from the sensor to a non-transitory computer readable medium. The method includes using the non-transitory computer readable medium to process the data from the sensor, and generating tracking information regarding positions of microsurgical instrumentation at the surgical site using the non-transitory computer readable medium.

In accordance with yet another aspect of the present invention, the method can include displaying the tracking information regarding positions of microsurgical instrumentation at the surgical site, generating a map from the tracking information, and displaying the map. The method also includes transmitting an alert to a user when a sensor is blocked for a predetermine period of time. The method can include receiving user input regarding the microsurgical instrumentation and the surgical site. Additionally, more than one sensor can be positioned around the surgical site. The sensors can be used during eye surgery, cochlear implant surgery, and/or a craniotomy procedure.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention provides a tracking system architecture for tracking surgical tools in a surgical field. The system architecture is integrated into a mask placed directly on the face of the patient. The system can combine multiple imaging and range finding technologies for tracking the eye and the surgical instrumentation. The system can be used to generate a three dimensional scene for use during the surgical procedure. Additionally, the system can incorporate a modular design to account for variable anatomy. The system described is for eye surgery applications. However, the system could also be used for other procedures such as cochlear implant or craniotomy.

Figure 1:
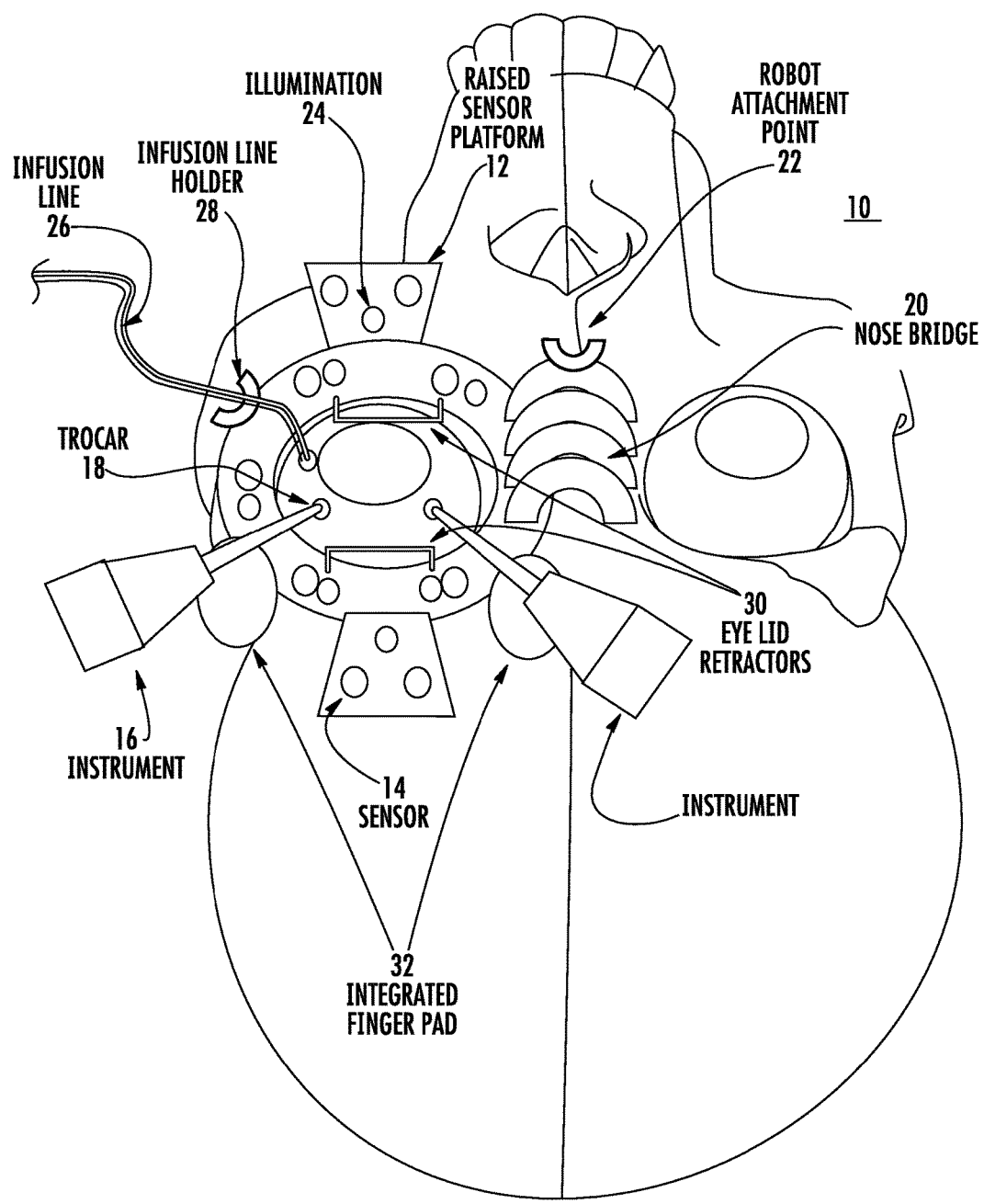
FIG. 1 illustrates a schematic diagram of a system for real-time tracking of the eye and the position of surgical instruments relative to each other and to the eye, according to an embodiment of the present invention.

FIG. 1 illustrates a schematic diagram of a system for tracking of microsurgical instrumentation, according to an embodiment of the present invention. As illustrated in FIG. 1, the system 10 includes a platform 12 outfitted with an array of sensors 14. The platform 12 can be raised from the surface of a face of the patient. The sensors are arranged in such a way, so as to provide sufficient tracking coverage for typical surgical procedures in the eye, while minimizing interference with typical surgical practice. The sensors 14 are configured such that they provide a depth map of the environment and are further able to extract human skeleton information. As illustrated in FIG. 1, the sensors 14 are positioned at multiple angles surrounding the eye to provide tracking coverage of the entire three-dimensional scene of the surgical field surrounding they eye. The sensors 14 are configured to transmit the tracking coverage information either wirelessly or via hardwires to a computing device (not shown). The computing device is used to process the tracking coverage information to obtain a model of the surgical scene. The computing device can take the form of any computing device known to or conceivable by one of skill in the art such as a PC, tablet, smartphone, or server computer. Standard multi-camera and multi-modal scene reconstruction methods known to one of skill in the art can be used to create a model of the scene. The three-dimensional scene data is then processed using standard volumetric data techniques to segment each instrument 16, trocar 18, fingers, lenses, eye surface, pupil, sclera, etc. The relative position of all of the instruments 16 or other items listed previously are inferred and are presented to other devices or software systems, such as the computing device described above.

As illustrated in FIG. 1, multiple sensors 14 can be positioned on the platform around the eye in order to provide redundancy in case of occlusions from surgical instruments, surgeons' hands and also from foreign matter, such as liquids or debris in the surgical field. In one potential embodiment of the present invention, it is possible to detect material on the lens, e.g. blood, using the computing device in communication with the sensors. For example, if the scene information is changing in all of the sensors except for one, it is possible that this sensor has foreign matter blocking its imaging path. Also, the sensor configuration can be used to generate tracking confidence based on coverage and correlation of the features in all the sensor data streams.

The sensors 14 can take the form of any suitable sensing device configured to transmit three-dimensional or lower dimensional projected scene data known to or conceivable by one of skill in the art. Examples of sensing technology that could be used to implement the present invention include, but are not limited to: RGB cameras (with compatible illumination), IR cameras (with compatible illumination), optical flow cameras, structured light methods (with compatible illumination), time-of-flight cameras, light detection and ranging (LADAR), sonar, ultrasound, optical coherence tomography, and/or electromagnetic sensing. Further, fish eye lenses used with any of the optical sensing modalities for a wide angle view. In cases where sensors conveying lower dimensional projected information (e.g., RGB or IR cameras) are used, then the information from two or more such sensors may be combined by triangulation methods known in the art to produce three dimensional information. Further information from multiple sensors with differing operating principles may be combined by methods known in the art to produce accurate three dimensional information. For example, information from electromagnetic or ultrasound sensors may be combined with multiple images from optical cameras. It should be noted however, that a sensor or tracking modality included as a component of the system of the present invention should not interfere with the visualization or any other instruments used to perform a surgery involving the system of the present invention.

Further, with respect to FIG. 1, the platform 12 can take a form resembling glasses with frames surrounding the eye. A nose bridge 20 aids in keeping the platform 12 positioned correctly. The nose bridge 20 can also include a robot attachment point 22 for securing a surgical robot to the system. The system can include an illumination source 24 also positioned on the platform 12. The illumination source 24 can include a number of distinct sources of illumination placed around the platform 12. An infusion line 26 and an infusion line holder 28 can also be included. In order to minimize instrumentation and to decrease the overall footprint of surgical equipment for the procedure, eye lid retractors 30 can be incorporated into the design, as illustrated in FIG. 1 or in any other manner known to or conceivable by one of skill in the art. In addition to the eye lid retractors 30, the system can also include an integrated surgical draping. Finger pads 32 can also be included to reduce hand fatigue and tremor.

Figure 2:
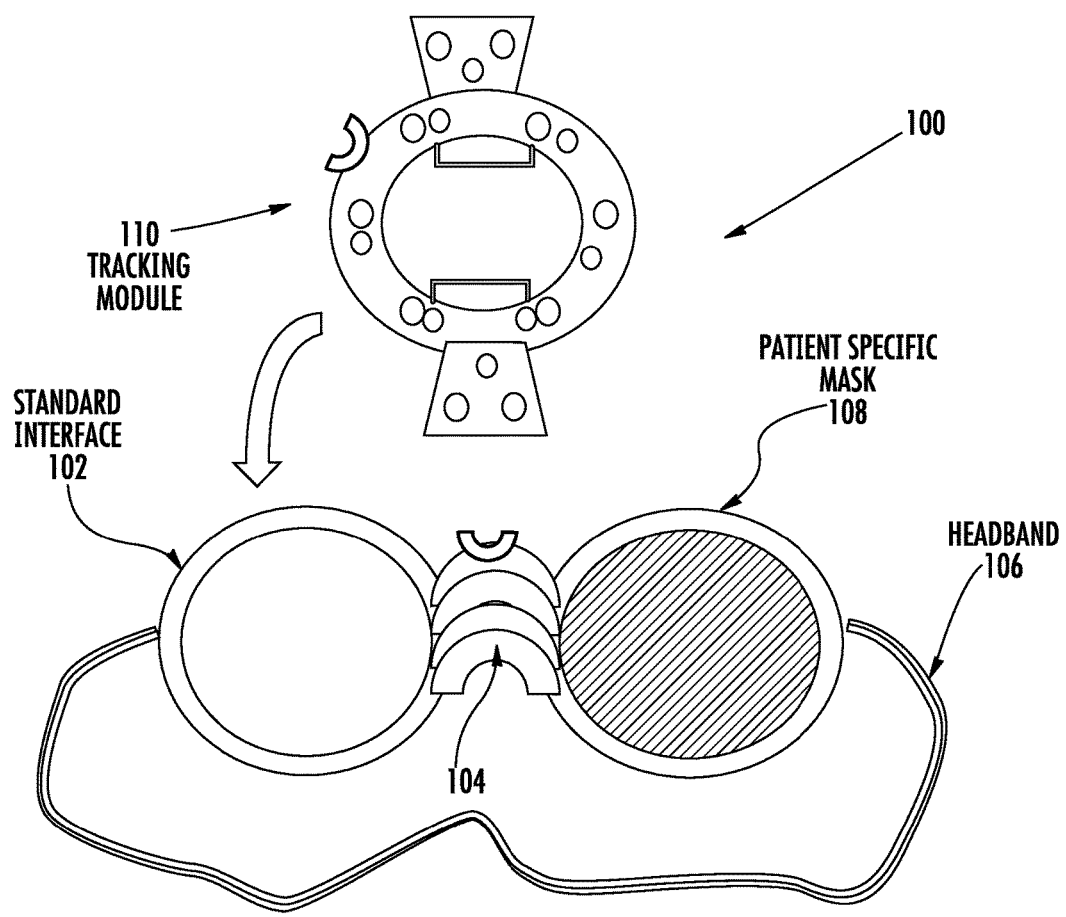
FIG. 2 illustrates a top down view of a system for real-time tracking of the eye and the position of surgical instruments relative to each other and the eye, according to an embodiment of the present invention.

FIG. 2 illustrates a top down view of a system for real-time tracking of the eye and the position of surgical instruments relative to each other and the eye, according to an embodiment of the present invention. As illustrated in FIG. 2, the system 100 includes an interface 102 having a nose bridge 104 and a headband 106 to secure the interface 102 to the patient's face. The interface 102 can include an eye mask 108 that can be inserted, moved, or removed, as necessitated by the surgical procedure. The platform 110 couples to the interface, and can be configured to couple to either a left eye segment of the interface, a right eye segment of the interface or both segments of the interface. The interface 102 and platform 110 can come in a variety of sizes in order to accommodate patients of different age and size. The design of the interface 102 and platform 110 can be ergonomic where necessary in order to allow for conventional surgical access. The design of the interface 102 and platform 110 can also be symmetrical or asymmetrical depending on accuracy and work envelope tracking coverage requirements. Additionally, the system 100 can be configured in parts in order to allow for easier and more complete sterilization of all of the components.

The system of the present invention described above with respect to FIGS. 1 and 2, provides information to microsurgical robots regarding their position with respect to the patient's anatomy to ensure safety and implementation of a number of desirable functions. One such function is ensuring an iso-centric rotation about the trocar (a remote center of motion). Another such function is automatic insertion of instruments into trocars in the surgical field. The system can also prevent unintentional collisions with other instruments/ robots and anatomy, as well as preventing excessive stress on the sclera by tracking the insertion points for feedback in control of a robot, such as a bimanual robot.

The system of the present invention can be used as a miniature navigation system to track imaging probes or other devices, while also providing feedback to the surgeon. In some embodiments, the feedback to the surgeon can take the form of a three-dimensional display. The redundancy provided by the system can also be used to reduce line-of-sight problems. The system can also include fiducial markers for instrument identification and for estimating the distance of the instrument inside the eye, in some embodiments.

The coordination of the instruments and sensors described herein is executed using a program written on a non-transitory computer readable medium to be loaded on and executed by the computing device disclosed above. The non-transitory computer readable medium can take any suitable form known to one of skill in the art. The non-transitory computer readable medium is understood to be any article of manufacture readable by a computer. Such non-transitory computer readable media includes, but is not limited to, magnetic media, such as floppy disk, flexible disk, hard, disk, reel-to-reel tape, cartridge tape, cassette tapes or cards, optical media such as CD-ROM, DVD, blu-ray, writable compact discs, magneto-optical media in disc, tape, or card form, and paper media such as punch cards or paper tape. Alternately, the program for executing the method and algorithms of the present invention can reside on a remote server or other networked device. The computing device can take the form of a PC, tablet, smartphone, processor, or any other suitable computing device known to or conceivable by one of skill in the art. The computing device can be incorporated directly into the imaging device or can be networked with the imaging device in a manner known to or conceivable by one of skill in the art.

The non-transitory computer readable medium is programmed to execute a method associated with the above described invention. The non-transitory computer readable medium is programmed to receive input from all of the sensors and any additional input that might be provided through a user interface by a physician, nurse, or assistant. The non-transitory computer readable medium processes the data received and creates a mapping or other representation of the surgical field in order to track different surgical instruments during a procedure. The mapping can be displayed in real time via the user interface. As the non-transitory computer readable medium receives input from, potentially, more than one sensor, the non-transitory computer readable medium also processes data from more than one sensor and can merge data from more than one source. The non-transitory computer readable medium also monitors the sensors to determine if useable input is being received from all sensors. For instance, a sensor might be blocked by a hand or body of a member of the surgical team. If a sensor remains blocked and does not provide any data for a predetermined period of time, the non-transitory computer readable medium can transmit an alert to a user interface of the computing device to notify surgical staff that one of the sensors is blocked and may need to be moved, cleaned, reattached, etc.

It should be noted that while the present invention is described with respect to a system for implementation of eye surgery, the present invention should not be considered limited to just one application. Additional uses include, but are not limited to, surgical skill assessment based on instrument motion and eye surgery process monitoring, and using environment/instrument tracking to monitor the surgical protocol for timely, correct sequence, and completion of tasks. The present invention can also be used for real time visualization of any surgical environment for operating room staff, tracking of freehand tools to warn of possible collisions with structures in a surgical field, and tool type detection to alert a surgeon that tools being used together are incompatible. It should also be noted that the system of the present invention does not rely on a magnetic field, which can be affected by metal in the surgical field. Therefore, the accuracy of such systems is suboptimal as compared to the present invention.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A system for tracking microsurgical instrumentation comprising:
   a platform configured to sit at a surgical site on a patient around an eye;
   a plurality of sensors configured to transmit three-dimensional projected scene data, wherein the plurality of sensors are positioned on the platform and configured to receive information regarding the surgical site and also further configured to transmit said information regarding the surgical site, wherein the plurality of sensors are further configured to receive and transmit information regarding placement of the microsurgical instrumentation about the surgical site and relative to the platform, further configured to receive and transmit a position of an instrument of the microsurgical instrumentation with respect to other instruments of the microsurgical instrumentation, and further configured to receive and transmit a position of the other instruments of the microsurgical instrumentation with respect to the platform, wherein the plurality of sensors are further configured to receive and transmit information about anatomy of the patient, and wherein the positioning of the plurality of sensors is configured to provide a complete volumetric scene of the surgical site, platform, placement of the microsurgical instrumentation, and anatomy of the patient;
   an illumination source positioned on the platform; and
   a computer configured to receive the information regarding the surgical site transmitted by the plurality of sensors and track the instrument of microsurgical instrumentation with respect to the platform, track the instrument of microsurgical instrumentation with respect to the other instruments of microsurgical instrumentation, track the anatomy of the patient, track the position of the other instruments of the microsurgical instrumentation with respect to the platform, and create the complete volumetric scene of the surgical site, platform, placement of the microsurgical instrumentation, and anatomy of the patient,
wherein the computer is further configured to generate a depth map of an environment of the surgical site and extract human skeleton information from the information transmitted by the plurality of sensors, and further configured to display the depth map in real-time.

2. The system of claim 1 wherein the plurality of sensors are positioned about the platform to create redundancy in the transmitted information.

3. The system of claim 1 wherein the system is configured for eye surgery.

4. The system of claim 3 wherein the platform is configured as an eye mask.

5. The system of claim 3 further comprising an eyelid retractor.

6. The system of claim 1 further comprising an attachment point for a surgical robot.

7. The system of claim 1 further comprising a finger rest.

8. The system of claim 1 wherein the computer is further configured to provide three-dimensional feedback regarding the surgical site.

9. A method for tracking microsurgical instrumentation at a surgical site comprising:
positioning a platform at the surgical site on a patient around an eye;
gathering data about the microsurgical instrumentation at the surgical site with a plurality of sensors configured to transmit three-dimensional projected scene data, wherein the plurality of sensors are positioned on the platform adjacent to the surgical site, wherein the plurality of sensors are configured to receive and transmit information about anatomy of the patient, and wherein the positioning of the plurality of sensors is configured to provide a complete volumetric scene of the surgical site, platform, placement of the microsurgical instrumentation, and anatomy of the patient is created;
transmitting data from the plurality of sensors to a non-transitory computer readable medium;
processing the data from the plurality of sensors using the non-transitory computer readable medium;
generating tracking information regarding positions of microsurgical instrumentation at the surgical site using the non-transitory computer readable medium;
generating tracking information regarding a position of a piece of the microsurgical instrumentation with respect to another piece of the microsurgical instrumentation, wherein the piece of microsurgical instrumentation and the another piece of microsurgical instrumentation are also tracked with respect to the platform positioned at the surgical site
illuminating the surgical site with an illumination source coupled to the platform;
creating the complete volumetric scene of the surgical site, platform, placement of the microsurgical instrumentation, and anatomy of the patient,
generating a depth map of an environment of the surgical site and extract human skeleton information from the information transmitted by the plurality of sensors; and
displaying the depth map in real-time.

10. The method of claim 9 further comprising displaying the tracking information regarding positions of microsurgical instrumentation at the surgical site.

11. The method of claim 9 further comprising transmitting an alert to a user when a sensor of the plurality of sensors is blocked for a predetermined period of time.

12. The method of claim 9 further comprising receiving user input regarding the microsurgical instrumentation and the surgical site.

13. The method of claim 9 wherein the surgical site comprises an eye surgery site.

* * * * *